(12) United States Patent
Simonette

(10) Patent No.: US 8,211,237 B2
(45) Date of Patent: Jul. 3, 2012

(54) CLEANING CONTACT LENSES VIA SONICATION

(76) Inventor: Rebecca A. Simonette, Houston, TX (US)

( * ) Notice: Subject to any disclaimer, the term of this patent is extended or adjusted under 35 U.S.C. 154(b) by 336 days.

(21) Appl. No.: 12/351,539

(22) Filed: Jan. 9, 2009

(65) Prior Publication Data

US 2010/0175711 A1    Jul. 15, 2010

Related U.S. Application Data

(63) Continuation of application No. 11/704,120, filed on Feb. 8, 2007, now Pat. No. 7,494,548.

(51) Int. Cl.
*B08B 3/12* (2006.01)
(52) U.S. Cl. ........ 134/1; 134/22.1; 134/225.1; 134/25.4
(58) Field of Classification Search .......................... None
See application file for complete search history.

(56) References Cited

U.S. PATENT DOCUMENTS

| | | | |
|---|---|---|---|
| 3,720,402 A | 3/1973 | Cummins et al. | |
| 3,851,861 A | 12/1974 | Cummins et al. | |
| 3,973,760 A | 8/1976 | Browning et al. | |
| 4,382,824 A | 5/1983 | Halleck | |
| 4,607,652 A | 8/1986 | Yung | |
| 4,697,605 A | 10/1987 | Yung | |
| 4,903,718 A * | 2/1990 | Sullivan | 134/184 |
| 4,991,609 A | 2/1991 | Browning | |
| 5,129,410 A | 7/1992 | Ifejika | |
| 5,178,173 A * | 1/1993 | Erickson et al. | 134/184 |
| 6,183,705 B1 | 2/2001 | Chang | |
| 6,193,806 B1 | 2/2001 | Reed | |

FOREIGN PATENT DOCUMENTS

| | | | |
|---|---|---|---|
| JP | 63-033726 | * | 2/1988 |
| JP | 09-225010 | * | 9/1997 |

* cited by examiner

*Primary Examiner* — Michael Kornakov
*Assistant Examiner* — Ryan Coleman
(74) *Attorney, Agent, or Firm* — Clifton W. Thompson

(57) ABSTRACT

Cleaning contact lenses by placing each contact lens in a daily use contact lens case with contact lens solution such as sterile saline or lens cleaning/disinfecting solution, placing the case in a liquid in a cleaning tank of an ultrasonic cleaning device operating at a frequency and power level sufficient to clean each lens in a convenient time period.

19 Claims, 1 Drawing Sheet

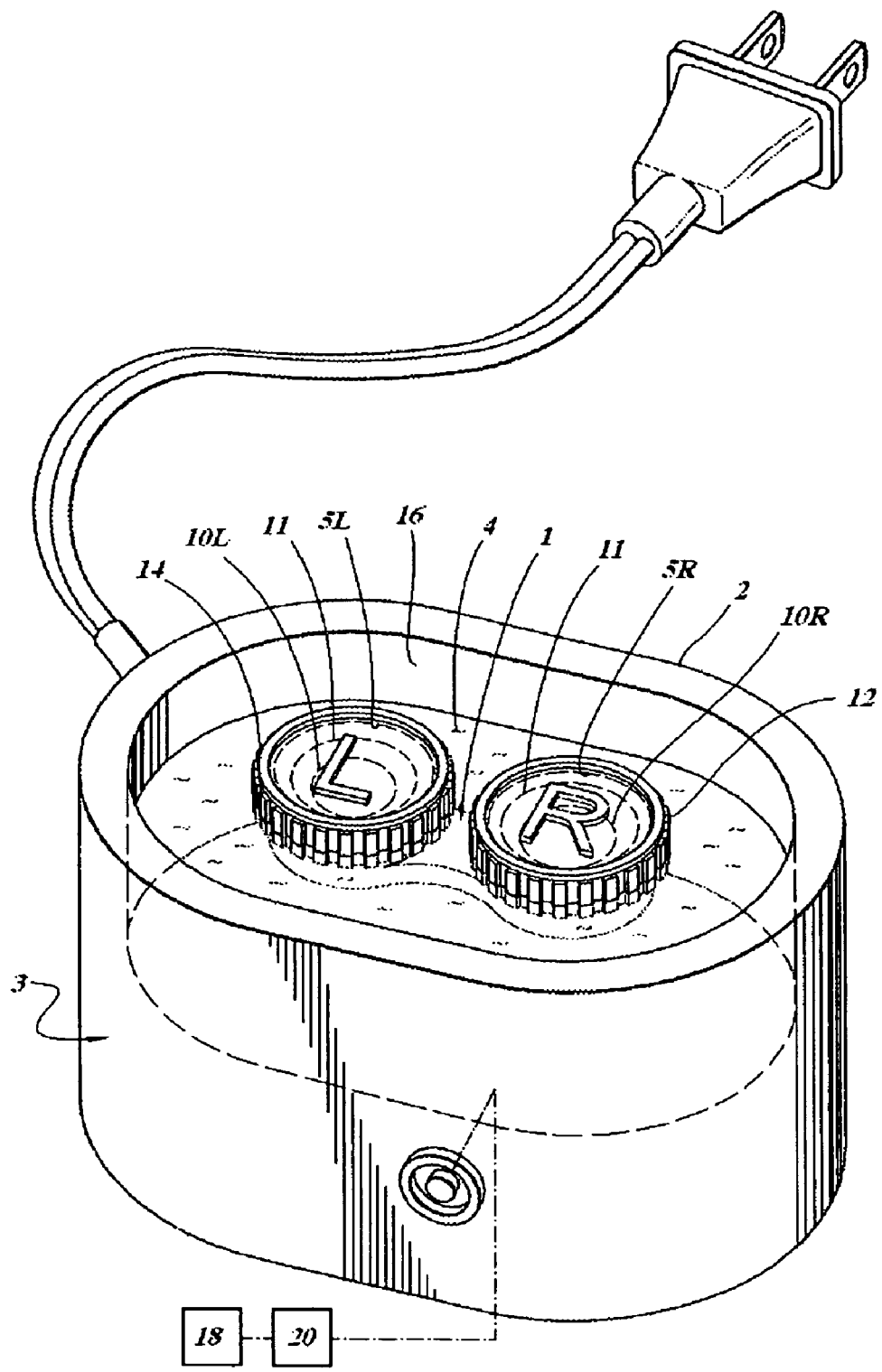

CLEANING CONTACT LENSES VIA SONICATION

APPLICATION DATA

This application is a continuation of U.S. patent application Ser. No. 11/704,120 filed Feb. 8, 2007, which issued as U.S. Pat. No. 7,494,548 B2 on Feb. 24, 2009.

BACKGROUND

There are many techniques for cleaning and sterilizing contact lenses. Contact lenses can be fragile and collect surface contaminants that diminish the usefulness of contact lenses. Moreover, many contact lens wearers do not comply with proper cleaning and handling of contact lenses.

Some wearers scrub their lenses with their fingers or use non-scrub cleaners and enzymatic drops or enzymatic soaking tablets to try to clean their contact lenses. Some of the enzymatic cleaners are made from porcine pancreatic enzymes, which are against dietary laws for some wearers. During the cleaning process wearers can have the misfortune of tearing their lenses.

Surface contaminants on contact lenses can be from external sources like dirty fingers, or airborne particles, or from eye discharge that can consist of protein deposits or lipid and mucoid products.

SUMMARY OF THE INVENTION

The invention in one embodiment comprises a method of cleaning a contact lens, including: a) placing a contact lens in a contact lens storage/carrying case with contact solution; b) sealing said case with the contact lens therein; b) placing the case in a sonicator with water; c) sonicating the water, contact lens case, contact solution, and contact lens; and d) removing said case from the sonicator; wherein said case is a liquid impermeable contact lens case configured so as to be robust and protect the lens for daily wear use and carrying about the person of a contact lens user consistent with configuration attributes of daily wear contact lens cases typically used by contact lens users, such as the typical conventional daily wear contact lens case described and illustrated herein.

BRIEF DESCRIPTION OF THE DRAWING FIGURE

FIG. 1 is a perspective view of an embodiment of the invention, illustrating a conventional daily-use contact lens case floating partially submerged in a liquid-filled cleaning tank of a sonicator during cleaning. A timer is shown schematically within the sonicator using a hidden line convention, and a contact lens and a contact lens fluid is shown within the contact lens case, also by hidden line convention.

DETAILED DESCRIPTION OF PREFERRED EMBODIMENT(S) OF THE INVENTION

The present invention concerns a process for cleaning contact lenses 10L, 10R. A conventional storage and carrying case 1, suitable for daily contact wearing use, is provided. The contact lenses are placed within their respective lens chambers 5L, 5R in the standard liquid impermeable contact lens storage case. The contact lenses are then covered with an aqueous medium such as sterile saline or contact lens cleaning and disinfecting solution 11. The right and left corresponding liquid impermeable covers 12, 14 of the filled contact lens chambers are placed over their respective chambers and securely fastened so the lenses are housed in a buoyant liquid impermeable manner. The contact lens case is then placed in the cleaning tank 16 within a housing 2 of an ultrasonic cleaning device 3, said cleaning tank being filled with a liquid 4, preferably water, so said liquid suspends said contact lens case 1. Said ultrasonic cleaning device 3 has a timer 18, and a switch 20 which activates it and initiates the production of ultrasonic waves. The strength of these waves depends on the power of said ultrasonic cleaning device 3.

Said timer 18, and switch 20 function to both turn on said ultrasonic cleaning device 3 and to automatically turn off said ultrasonic device after a set time has expired. Said contact lens case 1 is removed from the liquid 4 and can be left undisturbed until the user is ready to wear the lenses 10L, 10R; or the right and left corresponding nonporous covers 12, 14 of the filled contact lens chambers 5L, 5R, can be removed and the chambers can be refilled with new sterile saline or contact lens cleaning and disinfecting solution 11, and then recovered until use.

This new method of cleaning facilitates the cleaning and disinfecting process and improves the visual clarity of the lenses 10L, 10R for the wearer for the recommended life of the contact lenses. This is done in a manner that is simple, economical and quick. This method of cleaning, because of its simplicity and effectiveness, can help contact lens wearers remove unhealthy contaminants on the surface of the contact lenses. This improves the clarity of the contact lenses for the recommended life of the particular type of contact lenses, and also better protects the vision of the wearer.

In one embodiment the cleaning tank 16 is filled with a suitable aqueous medium such as water 4 to a fill level that allows for free movement of the standard two chambered liquid impermeable contact lens case 1. With the elimination of the need to have the contact lens container conform to a the ultrasonic unit, the design of the ultrasonic cleaner 3 can be simplified; various ultrasonic units readily available commercially (for example those set forth below), can be utilized, and accommodation of a great variety of sizes and shapes of contact lens cases is allowed. For this method, the contact lenses are removed from the wearers eyes and placed in the respective left and right chambers 5L, 5R of the standard lens case 1, then an aqueous medium 11 such as sterile saline or contact lens solution is added to cover the contact lenses. The covers 12, 14 of the standard lens chambers are tightened over each chamber so the contact lenses are secured within the contact lens case. The contact lens case is now liquid impermeable and buoyant. In the illustrated embodiment the contact lens case is suspended in a free-floating manner in the cleaning tank 16 of the ultrasonic device. In one embodiment, the ultrasonic device operates at 20 watts for a six-minute time span. At 117 watts, the contact lenses can be cleaned with a shortened time span of one minute in another embodiment.

This has been determined by experimenting with several different types of jewelry ultrasonic cleaners for home use and with ultrasonic cleaners manufactured for industry use. It has been determined that the jewelry cleaning unit model SI414 by SHARPER IMAGE stores, which operates at up to 20 watts can clean contact lenses in a 5-6 minute cycle. The company BRANSONIC makes several models of ultrasonic cleaners of varying shapes and sizes for industry use. Model B220 operates at up to 117 watts and cleans effectively in a 1-minute cycle. There are several ultrasonic units readily available for purchase that allow for rapid cleaning of contact lenses that are manufactured by various companies. The ultrasonic cleaning device 3 of the illustrated embodiment has a switch 20 that turns on the ultrasonic device with the timer 18 so that the ultrasonic vibrations turn off when the timing means counts down to the end of cleaning time. This is a typical feature that can be found on ultrasonic cleaning devices. When cleaning is completed, the wearer can put fresh sterile saline or fresh cleaning/disinfecting solution in the contact lens container or leave the lenses as they are and wear them at a later time.

This simple method cleans contact lenses 10L, 10R in an efficient, economical manner, maintaining the usefulness of the contact lenses and the comfort of the wearer. This method also helps to keep the contact lens storage case 1 clean. This method when used with sterile saline 11 only, without chemicals, is hypoallergenic and suited for people who develop allergies to the various over the counter contact lens chemical storage solutions and cleaning liquids.

This method of cleaning contact lenses using ultrasonic waves is simple, works well with water in the cleaning tank and only requires a small amount of sterile saline or cleaning or disinfecting solution 11. This method takes only a few minutes of time and is economical after the initial purchase of the ultrasonic cleaning device. This method can make use of most standard nonporous contact lens cases used for daily wear, storage and carrying. The technique has been found to work well in maintaining contact lens clarity and comfort. Additionally, this method helps to keep the contact lens storage container clean. This method may be of assistance to people who develop allergic reactions to chemicals found in over the counter contact lens cleaning and disinfecting solutions and wetting drops. This method is successful without relying on a subsequent heating cycle. The lenses are protected during the ultrasonic cleaning process by floating in a cushion of liquid within their liquid impermeable lens container.

What is claimed is:

1. A method of providing for cleaning of contact lenses, comprising:
   Providing a liquid-tight contact lens case configured for daily contact wearing use including lens storage and for carriage about the person of a contact lens wearer;
   providing a contact lens;
   providing a contact lens solution;
   providing a sonicator;
   placing the contact lens and said contact lens solution in said contact lens case;
   closing said contact lens case, further comprising the step of providing a liquid-tight seal isolating said lens and said solution within said case;
   placing the closed contact lens case in the sonicator;
   activating the sonicator for sufficient time to clean the lens within said liquid-tight contact lens case;
   removing said contact lens case from the sonicator;
   whereby the lens can be cleaned in a contact lens case configured for daily wear use, enabling a single such case to be used for both daily wear and cleaning of the lens, and also enabling improved cleaning of the lens and liquid-tight contact lens case and preservation of attributes of the lens using said liquid-tight contact lens case and a contact lens solution within said case in an amount accommodated within said case.

2. A method as set forth in claim 1, further comprising the steps of:
   using the liquid-tight contact lens case for both cleaning and for daily wearing use, whereby a case used for lens storage and carriage about the person of a lens wearer is cleaned at the same time a wearer's lens is cleaned;
   removing the lens from said liquid-tight contact case and preparing it for insertion in the eye as for daily wear;
   emptying said case;
   refilling said case with contact lens solution.

3. A method as set forth in claim 1, wherein the step of providing a sonicator further comprises the step of providing a sonicator that employs at least one of a) an ultrasonic cleaning frequency and b) a power level of at least 20 watts.

4. A method as set forth in claim 1, wherein the step of providing said contact lens solution further comprises the step of providing at least one of a sterile saline solution and a contact lens cleaning solution and a contact lens disinfecting solution.

5. A method as set forth in claim 1, wherein the step of providing a sonicator further comprises the step of providing a sonicator further comprising a timer, and further comprising the step of controlling sonication time using said timer.

6. A method of cleaning a contact lens, comprising: a) placing a contact lens in a contact lens storage case with contact solution; b) sealing the contact lens storage case with the contact lens therein; c) placing the contact lens case in a sonicator with water; d) sonicating the water, contact lens case, contact solution, and contact lens; and e) removing said contact lens case from the sonicator; wherein said contact lens case is a liquid impermeable contact lens case configured so as to protect the lens for daily wear use and carrying about the person of a contact lens user.

7. A method as set forth in claim 6, where said sonicator enables a cleaning power level of at least 20 watts.

8. A method in accordance with the method set forth in claim 6, further comprising the step of providing a sonicator configured to clean at an ultrasonic frequency.

9. A method in accordance with the method set forth in claim 6, further comprising the step of providing a contact lens case which, in combination with said lens and said solution enclosed therein, is buoyant in water.

10. A method in accordance with the method set forth in claim 6, further comprising the step of providing for sonication which further comprises a step selected from the following steps:
    a) coordinating cleaning time with sonicator power level so that longer cleaning time is associated with less power and shorter cleaning time is associated with higher power;
    b) using a lower cleaning power setting for sufficient time to clean the lens; and
    c) using a power level sufficiently high to clean the lens in under 6 minutes.

11. A method in accordance with the method set forth in claim 1, wherein the step of providing a liquid-tight contact lens storage case includes the further steps of providing two lens chambers in the case, each chamber being coverable by a removable cover which can be tightened down to provide an essentially liquid-impermeable seal.

12. A method in accordance with the method set forth in claim 1, further comprising the step of providing a sonicator that employs a liquid cleaning tank.

13. A method in accordance with the method set forth in claim 12, wherein the step of providing a sonicator that employs a liquid cleaning tank further comprises
    using a liquid in the cleaning tank consisting essentially of water.

14. A method in accordance with the method set forth in claim 1, further comprising the step of providing for sonication which further comprises a step selected from the following steps:

a) coordinating cleaning time with sonicator power level so that longer cleaning time is associated with less power and shorter cleaning time is associated with higher power;
b) using a lower cleaning power setting for sufficient time to clean the lens; and
c) using a power level sufficiently high to clean the lens in under 6 minutes.

15. A method in accordance with the method set forth in claim 1, further comprising the step of providing a liquid tight contact lens case that is buoyant in the liquid in the cleaning tank when closed with a lens and contact lens solution carried therein.

16. A method in accordance with the method set forth in claim 1, further comprising the step of providing said sonicator configured to enable cleaning a plurality of lenses at one time.

17. A method of providing a contact lens cleaning system, comprising
combining at least the following:
- a contact lens case, which can be of a configuration enabling daily use, having a compartment which can be sealed liquid-tight and is configured to receive and contain and protect a contact lens and a contact lens solution;
- a contact lens solution, which can comprise at least one of a) sterile saline solution b) lens cleaning solution and c) lens disinfectant solution;
- a sonicator, which can be an ultrasonic cleaner, said sonicator configured to receive a liquid in a liquid container portion into a kit; and
making said kit available for use as follows
a) place a contact lens in a contact lens storage case with contact solution;
b) seal the contact lens storage case with the contact lens therein;
c) place the contact lens case in a sonicator with said liquid;
d) sonicate the liquid, contact lens case, contact solution, and contact lens; and
e) remove said contact lens case from the sonicator;
wherein said contact lens case protects the lens for daily wear use and carrying about the person of a contact lens user.

18. A method of providing a contact lens cleaning system as set forth in claim 17, further comprising the steps of
combining with other kit items a contact lens; and,
making same available for use.

19. A method of providing a contact lens cleaning system as set forth in claim 17, further comprising at least one further step from the following steps:
in said combining step, the further step of providing a sonicator that can operate at a power level of at least 20 watts; and,
in said combining step, the further step of providing a sonicator that can operate at an ultrasonic frequency.

* * * * *